US00PP37361P3

(12) United States Plant Patent
van Haaster

(10) Patent No.: US PP37,361 P3
(45) Date of Patent: Apr. 7, 2026

(54) DAHLIA PLANT NAMED 'DDAHCHRDFL'

(50) Latin Name: ***Dahlia* hybrid**
Varietal Denomination: DDAHCHRDFL

(71) Applicant: Ans van Haaster, Hillegom (NL)

(72) Inventor: Ans van Haaster, Hillegom (NL)

( * ) Notice: Subject to any disclaimer, the term of this patent is extended or adjusted under 35 U.S.C. 154(b) by 0 days.

(21) Appl. No.: 18/896,973

(22) Filed: Sep. 26, 2024

(65) Prior Publication Data

US 2026/0090490 P1 Mar. 26, 2026

(51) Int. Cl.
*A01H 6/14* (2018.01)

(52) U.S. Cl.
USPC ..... Plt./321

(58) Field of Classification Search
USPC ..... Plt./321
See application file for complete search history.

*Primary Examiner* — Shubo Zhou
*Assistant Examiner* — Zachariah Allan Kay

(57) ABSTRACT

A new and distinct cultivar of *Dahlia* plant named 'DDAHCHRDFL' is disclosed, characterized by abundant red and yellow colored double flowers, dark green foliage, and an upright habit. The new variety is a *Dahlia*, typically produced as an ornamental plant.

2 Drawing Sheets

Figure 1:
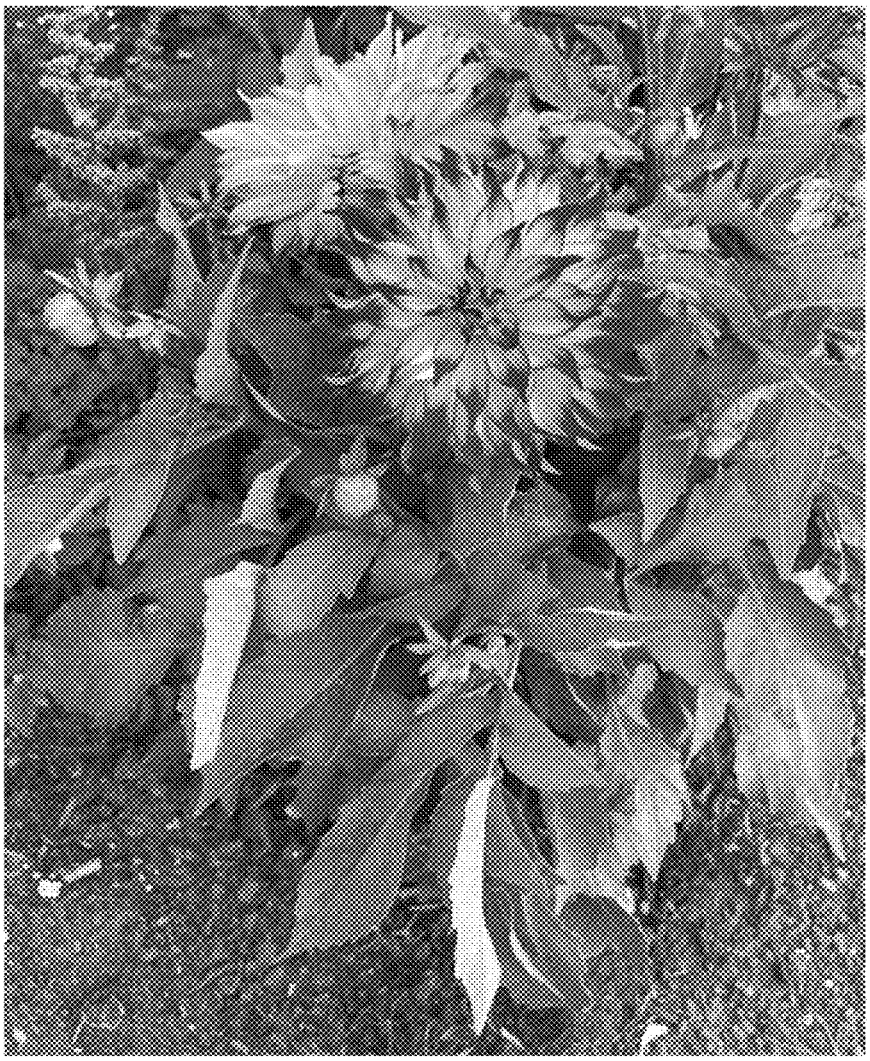

Latin name of the genus and species: *Dahlia* hybrid.
Variety denomination: 'DDAHCHRDFL'.

BACKGROUND OF THE INVENTION

The new *Dahlia* cultivar is a product of a planned breeding program conducted by the inventor, Ans van Haaster in Hillegom, the Netherlands. The objective of the breeding program was to produce useful new *Dahlia* varieties for ornamental horticultural production. The crossing resulting in this new variety was made in August 2020.

The seed parent is the unpatented variety *Dahlia* 'Hypnotica Red'. The pollen parent is the unpatented variety *Dahlia* 'Hypnotica Icarus'. The new variety was discovered in August 2021 by the inventor in a group of seedlings in Hillegom, the Netherlands. Asexual propagation of *Dahlia* was performed by vegetative cuttings in September 2021, at the same location in Hillegom, the Netherlands. After selection of the new variety, extensive confidential testing has been performed to determine and define the desirable characteristics of the new variety.

SUMMARY OF THE INVENTION

The cultivar 'DDAHCHRDFL' has not been observed under all possible environmental conditions. The phenotype may vary somewhat with variations in environment such as temperature, day length, and light intensity, without, however, any variance in genotype.

The following traits have been repeatedly observed and are determined to be the unique characteristics of 'DDAHCHRDFL'. These characteristics in combination distinguish 'DDAHCHRDFL' as a new and distinct *Dahlia* cultivar:

1. Yellow flower petals with bright red petal tips. Petals becoming more yellow with age.
2. Distinctly wavy petals.
3. Abundant flowering.

PARENT COMPARISONS

Plants of 'DDAHCHRDFL' are similar in some horticultural characteristics to the seed parent. The new variety, however, differs in the following:

1. Flower color of the new variety is red and yellow, while flower color of the seed parent is solid red.
2. Plants of the new variety are not as vigorous as plants of the seed parent.
3. Petal aspect of the new variety is wavy, while petals of the seed parent is round.
4. Flowers of the new variety are larger than flowers of the seed parent.

Plants of 'DDAHCHRDFL' are similar in some horticultural characteristics to the pollen parent. The new variety, however, differs in the following:

1. Petal aspect of the new variety is wavy, while petals of the pollen parent are more pointed and spiked.
2. Young flower color of the new variety is red in the center with a bit of yellow, while the young flower color of the pollen parent is spread more evenly.

COMMERCIAL COMPARISONS

Plants of 'DDAHCHRDFL' are similar in some horticultural characteristics to the variety *Dahlia* 'Labella Maggiore Fun Flame', unpatented. The new variety, however, differs in the following:

1. Flower color of the new variety is red and yellow, while flower color of this comparator is more orange.
2. Petal aspect of the new variety is wavy, while petals of this comparator is more straight.
3. Flower stems of the new variety are shorter than flower stems of this comparator.

Plants of 'DDAHCHRDFL' are similar in some horticultural characteristics to the variety *Dahlia* 'Labella Maggiore Fun Fire', unpatented. The new variety, however, differs in the following:

1. Petal aspect of the new variety is wavy, while petals of this comparator is more pointed.
2. Flower color of the new variety is red and yellow, while flower color of this comparator is darker red.

3. Plants of the new variety are not as tall and lanky as plants of this comparator.

BRIEF DESCRIPTION OF THE PHOTOGRAPHS

The accompanying photograph in FIG. 1 illustrates in full color a typical plant of 'DDAHCHRDFL' 80 days from planting, grown in a 15 cm pot.

Figure 2:
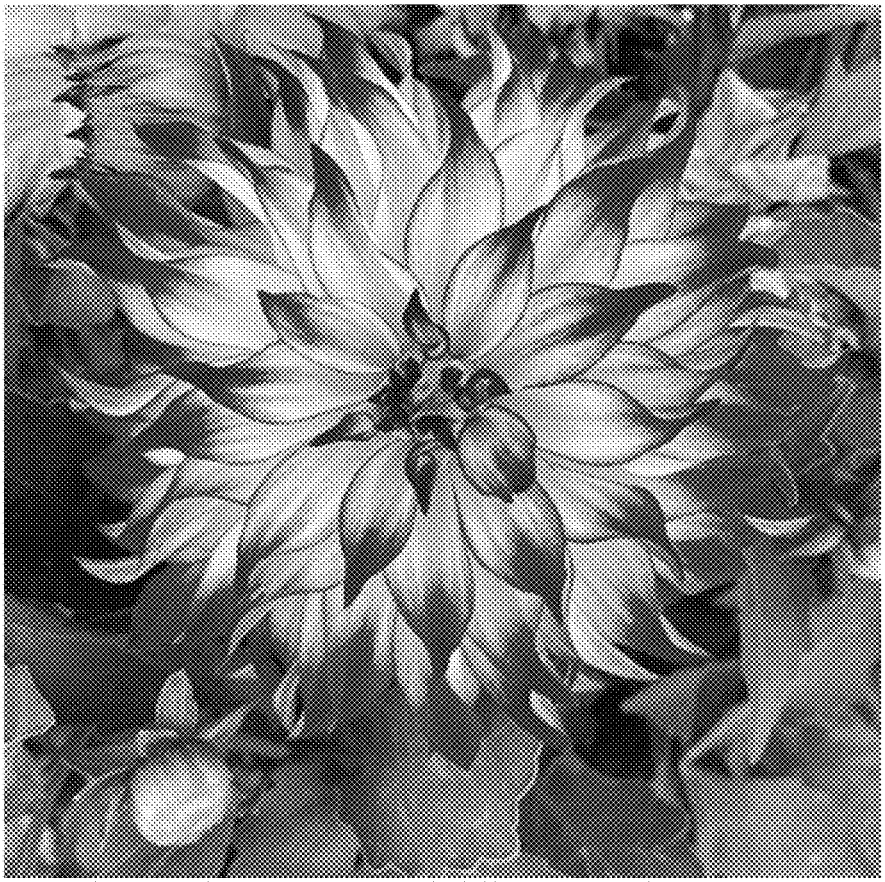

FIG. 2 illustrates a closer view of a typical flower of the new variety.

The photographs were taken using conventional techniques and although colors may appear different from actual colors due to light reflectance it is as accurate as possible by conventional photographic techniques.

DETAILED BOTANICAL DESCRIPTION

In the following description, color references are made to The Royal Horticultural Society Mini Colour Chart 2005 except where general terms of ordinary dictionary significance are used. The following observations and measurements describe 'DDAHCHRDFL' plants grown in a plastic tunnel in Hillegom, the Netherlands, under natural lighting. Measurements were taken August 2024. The growing temperature ranged from approximately 15° C. to 32° C. during the days, 8° C. to 20° C. during the nights. Measurements and numerical values represent averages of typical plant types.

Botanical classification: *Dahlia* hybrid 'DDAHCHRDFL'.

PROPAGATION

Propagation method: Vegetative cuttings.

Time to initiate rooting: 8 to 15 days in summer; 12 to 17 days in winter.

Root description: Fibrous and relatively shallow in the early stages of development. Roots grow more complex as the plant matures.

Tuber description: Skin firm and relatively thin, colored light brown (199A). Inner flesh moist and firm, colored white (155A).

PLANT

Age of plant described: Approximately 80 days from planting.

Growth habit: Upright.

Pot size of plant described: 13 cm.

Height: 42 cm.

Plant spread: 45 cm.

Branching characteristics:

Length of lateral branches: 16 cm.

Quantity of lateral branches: 10 per main stem.

Characteristics of primary lateral branches:

- *Diameter.*—0.8 cm.
- *Color.*—RHS Green 138B.
- *Texture.*—Smooth.
- *Strength.*—Strong. Neither brittle nor soft, resisting breakage.

Internode length: 6.5 cm.

FOLIAGE

Leaf:

- *Arrangement.*—Alternate.
- *Quantity.*—Approximately 7 per branch.
- *Average length.*—13.5 cm.
- *Average width.*—12 cm.
- *Pubescence.*—None.
- *Shape.*—Triangle.
- *Apex.*—Acuminate.
- *Base.*—Rounded, slightly cordate.
- *Margin.*—Serrate.
- *Texture.*—Smooth, both sides.
- *Aspect.*—Slightly undulating.
- *Color.*—Young, Upper side: RHS Green 138B. Young, Under side: RHS Green 138C. Mature, Upper side: RHS Green 138A. Mature, Under side: RHS Green 138B.
- *Venation.*—Pattern: Reticulate. Color, upper side: RHS Green 138B. Color, under side: RHS Green 138C.

Petiole:

- *Length.*—3 cm.
- *Diameter.*—0.2 cm.
- *Color.*—RHS Green 137A.
- *Texture.*—Smooth.

Stipule:

- *Length.*—3 cm.
- *Diameter.*—1 cm.
- *Color.*—RHS Green 138B.
- *Texture.*—Smooth.

FLOWER

Natural flowering season: Summer to autumn.

Days to flowering from rooted cutting: 55 days.

Inflorescence and flower type and habit: Decorative *Dahlia* type.

Rate of flower opening: 6 to 11 days from bud to fully opened flower.

Flower longevity on plant: 20 days.

Persistent or self-cleaning: Persistent.

Bud:

- *Shape.*—Round.
- *Length.*—1.7 cm.
- *Diameter.*—2 cm.
- *Color.*—RHS Yellow-Green 154A very lightly flushed Purple-Red 61B.

Flower size:

- *Diameter.*—12 cm.
- *Depth.*—4.5 cm.

Petals:

- *Arrangement.*—Double flower, radial symmetry.
- *Length.*—6 cm.
- *Width.*—1.8 cm.
- *Quantity.*—124.
- *Texture.*—Smooth.
- *Apex.*—Round.
- *Base.*—Pointed.
- *Shape.*—Oval, wavy.
- *Margin.*—Entire.
- *Color.*—When Opening, Upper Surface: RHS Red-Purple 60A apical section and Yellow 5A basal section. When Opening, Lower Surface: RHS Red-Purple 60B apical section and Yellow 5B basal section. Fully Opened, Upper Surface: RHS Red-Purple 61A apical section and Yellow 5B basal section. Fully Opened, Lower Surface RHS Red-Purple 61B apical section and Yellow 5B basal section.

Sepals:
*Quantity per flower.*—6.
*Shape*.—Oval.
*Length.*—1.5 cm.
*Width.*—0.5 cm.
*Apex*.—Round.
*Base*.—Pointed.
*Margin*.—Entire.
*Color*.—RHS Yellow-Green 147B.
Peduncles: None.
Fragrance: Soft floral scent.

REPRODUCTIVE ORGANS

Androecium:
Stamens:
*Number.*—42.
Anthers:
*Shape*.—Elongated, narrow.
*Length*.—About 0.05 cm.
*Color*.—RHS Yellow 9A.
*Pollen*.—Color: RHS Yellow 9A. Quantity: Abundant.
Gynoecium:
Pistil:
*Number.*—42.
*Length.*—1.8 cm.
*Style*.—Shape: V-shaped. Length: 1 cm. Color: RHS Yellow 9B.
*Stigma*.—Shape: V-shaped. Color: RHS Yellow 9B. Ovary Color: RHS Yellow 9B.

OTHER CHARACTERISTICS

Seeds and fruits: None observed.
Disease/pest resistance: Neither resistance nor susceptibility to typical *Dahlia* pests and diseases observed.
Temperature tolerance: Tolerant of temperatures from 1° to 38° C.

What is claimed is:

1. A new and distinct cultivar of *Dahlia* plant named 'DDAHCHRDFL' as herein illustrated and described.

* * * * *